United States Patent [19]

Carbon et al.

[11] Patent Number: 4,464,472

[45] Date of Patent: Aug. 7, 1984

[54] CONSTRUCTION AND USE OF FUNCTIONAL MINICHROMOSOMES

[75] Inventors: John A. Carbon; Louise B. Clarke, both of Santa Barbara, Calif.

[73] Assignee: The Regents of the University of California, Berkeley, Calif.

[21] Appl. No.: 452,275

[22] Filed: Dec. 22, 1982

Related U.S. Application Data

[63] Continuation of Ser. No. 185,453, Sep. 9, 1980, abandoned.

[51] Int. Cl.$^3$ .................. C12N 1/16; C12P 21/00; C12P 21/02; C12P 19/34
[52] U.S. Cl. ................................ 435/255; 435/68; 435/70; 435/91
[58] Field of Search .............. 435/68, 70, 91, 255, 435/172, 317, 256; 536/27

[56] References Cited

PUBLICATIONS

Ruddle et al.: Nature 294, 115, (1981).
Lewin: *Gene Expression,* vol. 2, second edition, John Wiley & Sons, New York, 1980, pp. 242–252.
Klobutcher et al.: Nature 280, 657, (1979).
Hinnen et al.: Proc. Natl. Acad. Sci., USA: 75, 1929, (1978).
Struhl et al.: Proc. Natl. Acad. Sci., USA: 76, 1035, (1979).

*Primary Examiner*—Thomas G. Wiseman
*Assistant Examiner*—James Martinell
*Attorney, Agent, or Firm*—Bertram I. Rowland

[57] ABSTRACT

Functioning eukaryotic minichromosomes containing a centromere, at least one replicating site, and at least one functioning structural gene. Centromeres are obtained from a host chromosome and used as a genetic unit in combination with an autonomously replicating segment for high frequency stable transformation of host and other eukaryotic cells. The transformed eukaryotic cells can be cultivated through repeated passages without significant loss of the minichromosome and continued expression of the structural genes present in the minichromosome.

3 Claims, No Drawings

CONSTRUCTION AND USE OF FUNCTIONAL MINICHROMOSOMES

The invention described herein was made in the course of or under a grant from the National Cancer Institute, National Institute of Health (Grant No. CA-11034).

This is a continuation of pending patent application Ser. No. 185,453, now abandoned, filed Sept. 9, 1980.

BACKGROUND OF THE INVENTION

1. Field of the Invention

The ability to introduce genetic material into a functioning cell, where the genetic material is then expressed, has opened up a phantasmorgia of opportunities. With each new discovery of the manner in which the replication and expression of genetic material is naturally controlled, there is an ever increasing capability of modifying cells to desired useful ends.

Much of the original work with hybrid DNA technology concerned prokaryotic organisms. For the most part, molecular biology has looked to prokaryotic organisms for an understanding of genetic control of cell growth and proliferation. However, for many purposes, it will be desirable or necessary to transform eukaryotic cells. Much less is known of the manner of genetic replication and regulation in eukaryotic cells. One distinct difference between eukaryotes and prokaryotes for the purposes of hybrid DNA technology is the substantial absence in most eukaryotes of plasmids or other extrachromosomal DNA.

In transforming a cell, it is not sufficient that an individual cell accept the genetic material. It is also necessary that upon mitosis, the progency cell have retained the introduced genetic material. In order for this to occur, at each mitotic event, the introduced genetic material must be replicated and upon division, one copy be retained by each cell. Therefore, when introducing genetic material into a eukaryotic cell, means must be provided involving the coding which provides for replication of the genetic material and stable maintenance upon mitosis.

2. Description of the Prior Art

The following references concern autonomously replicating segments and centromeres: Kingsman et al., Gene, 7 (1979) 141-152; Hsiao and Carbon, Proc. Natl. Acad. Sci. USA 76, 3829-3833 (1979); Clarke and Carbon, ibid 77, 2173-2177 (1980) (Note particularly, Note added in proof, on page 2177) and an Abstract at the Alfred Benzon Symposium, June, 1980, Copenhagen, Denmark. Also note the reference cited in the aforestated references, particularly Hinnen et al., Proc. Natl. Acad. Sci. USA 75, 1929-1933 (1978) and Struhl et al., ibid 76 1035-1039 (1979).

SUMMARY OF THE INVENTION

Hybrid DNA is provided for efficient stable transformation of eukaryotic cells. The hybrid DNA is comprised of (1) one or more DNA sequences which code for the initiation of replication of DNA (ars); (2) a DNA segment which codes for chromosome-like meiotic and mitotic activity of the hybrid DNA; and (3) at least one additional gene, usually a structural gene, expressing a phenotypic property. Conventionally, the DNA segment referred to in (2) above can be obtained as a centromere, by cleaving a eukaryotic chromosome on opposite sides of the chromosomal centromere. When the centromere containing segment lacks an ars gene, the centromere containing segment is combined with an ars, normally in combination with one or more genes, such as structural genes, genes coding for binding sites, such as prokaryotic origins, promoters, operators, initiation and termination sites, and the like to provide for linear or circular DNA, which acts as a chromosome and is referred to as a minichromosome.

Eukaryotic cells, which may or may not have been the host source for the centromere and/or the ars, may be stably transformed with the minichromosome. The minichromosome is stably retained through many generations with continued expression of the genes present on the minichromosome.

DESCRIPTION OF THE SPECIFIC EMBODIMENTS

Hydrid DNA is provided for transforming eukaryotic cells efficiently and stably. The hybrid DNA is stably maintained by the cells through many generations with continued expression of the genes present in the hybrid DNA. The hybrid DNA has three prime components: (1) a DNA segment, referred to as a centromere, which codes for chromosome-like activity during meiosis and mitosis; (2) a DNA sequence which serves as a replication site for replication of the DNA to produce an identical hybrid DNA; and (3) other DNA sequences including genes, such as structural genes or regulatory genes e.g, binding sites, such as promoters, operators, initiation sites, and terminator sites, and the like. For convenience only, the hybrid DNA will be referred to as a minichromosome. The term minichromosome is descriptive of many properties of the hybrid DNA which are mimetic of chromosomes.

In describing the minichromosomes of this invention, the individual components will first be considered: Namely the segment conferring the centromere activity; the sequence conferring the replication site; and other genes which contribute properties to transformed cells.

Centromere

The centromere is the junction between the two arms of a chromosome to which the spindle fibers attach, either directly or indirectly, during mitosis and meiosis. Thus, the centromere acts to orient the chromosome during cell splitting, so that the two copies of the chromosome are directed to opposite poles of the cell prior to splitting into two progeny. The centromere also acts as a binding site for binding the chromosome to the spindle, thus insuring that each daughter cell receives a copy of the chromosome.

Each of the chromosomes of a eukaryote may have a centromere of different composition. For the most part, the centromeres will be relatively small, usually smaller than about 2kbp, usually less than about 1.6kbp and may function with as few as 0.2kbp, more usually as few as 0.5kbp. For the most part, the centromere segment does not have long repetitive segments as observed with heterochromatin.

The centromere may be obtained from any eukaryotic host. Eukaryotic hosts include plants, insects, molds, fungi, mammals and the like. Of particular interest are plants, particularly food crops, fruit trees, and wood trees; fungi, such as mushrooms, yeast, Streptomyces or other antibiotic producing species; mammals, such as domestic animals and humans; and birds, such as domestic poultry.

There are a number of different ways to obtain centromeres. Initially, the centromere will normally be obtained from a host chromosome. Desirably, the host chromosome has been mapped so as to establish an area which functions as the centromere and is bordered by restriction sites. The area defined as the centromere frequently can be detected by the substantial absence of recombination events in the vicinity of the centromere. By appropriate mapping, one can define structural genes on opposite sides of the centromere and restriction sites which allow for cleavage of the chromosome to produce a segment including at least one structural gene and preferably both structural genes. The structural genes serve as markers, since the expression of the structural genes in a clone requires the presence of the centromere.

The fragments will generally be less than ten percent in number of base pairs of the chromosome from which the centromere containing fragment was derived. Fragments may then be formed by restriction enzyme cleavage. The fragments may be inserted into a shuttle vector containing a prokaryotic replication site and a eukaryotic chromosomal replicator. By transforming a prokaryote auxotrophic mutant which is complemented by at least one of the structural genes adjacent the centromere one can select for clones having a high probability of having the centromere DNA sequence. Selective medium will permit selection of the transformed clones.

The eukaryotic fragments inserted into the shuttle vector are then excised at the restriction sites; the resulting mixture of eukaryotic segments will have a greatly enhanced concentration of centromere containing segments. The mixture of DNA fragments may now be inserted in the same shuttle vector or a different vector having a replicating site for the host to be transformed, which may or may not be the same host from which the centromere was obtained. Desirably, the host should be an auxotroph for one of the structural genes associated with the centromere to allow for rapid selection of host transformed with the hybrid DNA containing the structural gene. By cultivating the host through a number of generations, transformed cells having plasmid lacking the centromere will be unstable and reject the plasmid. Those cells which retain the markers and are prototrophic in the marker will have plasmids containing the centromere. Therefore, it is not necessary to employ an auxotrophic mutant, it will be sufficient to employ a phenotypic marker, particularly one allowing for selection.

The plasmids are isolated from the cells and by employing overlap hydridization, the DNA sequence providing the centromere function is identified. The centromere may then be isolated substantially free of the genes immediately adjacent the centromere in the chromosome from which the centromere was derived. In this way, one can have a DNA segment which provides the centromere function and can be bonded to a wide variety of structural genes, operators, binding sites, regulating genes, or the like, in addition to the one or more replicating sites.

Once the centromere segment has been isolated, the segment may be sequenced and synthesized. Synthetic techniques for preparing single stranded DNA or double stranded DNA have been amply described in the literature. See, for example, Wu (1978) Ann. Rev. of Biochem. 47, 607 and articles cited therein. Alternatively, the sequence may be used as a template for synthesis in vitro, employing a partial lysate or soluble enzyme system. Therefore, the isolation and sequencing of the centromere as described above opens up a variety of avenues for its subsequent replication.

Replication Site

In order to have stable mitotic maintenance, a replication site in combination with the centromere segment is necessary. The replication site is the DNA sequence which is recognized by the enzymes and proteins involved in replication of the DNA duplex. The replication site can be initially obtained by genomic cloning. The chromosomes of the host can be fragmented either mechanically or preferably by restriction enzymes. The fragments may then be inserted into an appropriate vector, which may or may not have one or more genetic markers. Particularly, the vector should lack a replication site which would allow for replication in the eukaryotic host to be transformed.

After transformation and passage through a number of generations, one can select for the presence of the marker. Only those cells containing a DNA fragment having a replication site will be able to retain the plasmid to any detectable degree. The cells may then be harvested, lysed, and the plasmid isolated. The inserted DNA fragment may be excised and used for introduction of the replication site in combination with the centromere. The replication site will hereinafter be referred to as an autonomously replicating segment, ars.

Where an autonomously replicating segment is known to be associated with a structural gene, the structural gene may be employed as a marker. By transforming hosts which are auxotrophic for the product expressed by the marker, one can select for transformed cells which are able to grow in a selective medium. Only those cells having the combination of the ars and marker will survive in the selective medium.

Once the ars has been isolated as part of a larger fragment, the fragment may be reduced in size, employing endo- or exonucleases, capable of cleavage or processive oligonucleotide removal. The resulting fragments may be inserted in an appropriate vector and used for transformation. Once again, only those cells which are transformed with a functional ars will be able to retain the plasmid in selective medium. If the vector includes a centromere, nonselective medium may be employed, since a plamid containing only the ars and not the centromere is mitotically unstable.

The ars fragment may or may not be joined to the native genes on opposite sides of the ars when combined with the centromere to form the minichromosome. When the ars employed is free of the native functional genes, it will normally be less than about 1kbp, usually less than about 0.5kbp and may be as small as 0.2kbp.

As part of the minichromosome, the ars may or may not be derived from the same host as the centromere was derived from, nor from the same cell source as the host cell to be transformed by the minichromosome.

Minichromosome

The minichromosome is a combination of a DNA segment fulfilling a centromeric function, a replicating site, and one or more genes, including regulatory genes and structural genes, which are to be expressed by the transformed host cell. The minichromosome can be prepared stepwise by insertion of the various DNA segments into a circular plasmid. Conveniently, a circular plasmid is employed which has been mapped for restriction sites. Frequently, the plasmid will have one or more markers, whose activity may be retained or lost by employment of a particular restriction enzyme. In this manner, the minichromosome can be prepared having predefined markers, and followed stepwise by the gain and/or loss of particular markers.

Various techniques can be used for insertion of the DNA segments containing the desired genes into circular DNA. Blunt end cleavage can be employed employing poly(dN)poly(dN') connectors (where N and N' are complementary bases), cohesive ends can be prepared using restriction enzymes providing staggered ends, or exonucleases may be used to remove portions of one of the DNA chains to expose areas of complementarity. The various DNA segments may be added together or sequentially with appropriate connectors to allow for annealing and subsequent ligation. The resulting minichromosome may then be used in accordance with known techniques to transform eukaryotic cells.

The minichromosomes can include a wide variety of genes to provide new or enhanced genetic capabilities to the transformed host. Structural genes can be provided which code for enzymes which are native or foreign to the transformed host, for regulatory proteins e.g. hormones, which are native or foreign to the host or production of various organic chemicals by transformation of a nonproteinaceous substrate, which may be a normal or abnormal substrate for the transformed host. The minichromosomes can be used to modify genetic traits of hosts, such as changing host nutrient or environmental requirements, response to invasive organisms or providing absent genetic capabilities.

Transformation can be achieved by using calcium shock, by exposing host cell spheroplasts to the plasmid DNA under conditions favoring spheroplast fusion and then plating the spheroplast in regeneration agar selecting for the desired phenotype; or other conventional techniques.

The transformed host cells may then be grown on selective or nonselective medium. While the minichromosome has mitotic stability, it is well established that aneuploid cells will frequently lose one of the chromosomes. Since the minichromosome in nonselective medium will not be necessary for viability, loss of the minichromosome will not adversely affect the viability of the resulting "wild type" of cell. Therefore, it will usually be desirable to have a marker on the minichromosome which provides for selective pressure for the transformed host cells.

The nature of the marker may be varied widely providing for resistance to a cell growth inhibitor; complementation of an auxotrophic mutation in the transformed host; morphologic change; or the like.

The minichromosomes can be used for a wide variety of purposes. For example, the minichromosomes can be used for transforming yeast, where the yeast cells can then be used for commercial production of a wide variety of products. Not only can proteinaceous products be produced, as described above, but the yeast cells can be used to process chemicals, degrade waste or other materials, or be harvested as a food product. In other than microorganisms, cells can be transformed for complementation of a mutation, providing for expression of an exogenous gene to produce a foreign protein, for the diagnosis and treatment of disease, and the like. In addition, the minichromosomes can serve as a useful source for DNA fragments to be used in conjunction with research efforts, modification of other cells, such as the production of transposable elements, and the like.

The following examples are offered by way of illustration and not by way of limitation.

EXPERIMENTAL

The following data is taken from Clarke and Carbon, supra. References as to the strains, DNA segments, and vectors will be found in that reference and are not cited here. The disclosure of that reference concerning the manner of preparing the DNA segments, plasmids and transformation is incorporated herein by reference and the following description highlights the description in the article and is provided primarily for convenience.

E. coli strains used are the following: W3110 (trpC1117) and SF8 (C600 hsdM hsdR recBC lopll); S. cerevesiae strains used are: RH218 (a trp1 gal2 SUC2 mal CUP1); 6204-18A (α leu2-3, 112 cdc10 thr can1); XSB 52-23C (α leu2 cdc10 trp1 gal) constructed by crossing RH218 with 6204-18A, and X2180-1A (a SUC2 mal gal2 CUP1).

Yeast DNA for construction of hybrid plasmid colony banks was prepared from strain X2180-1A. The new colony bank employing the shuttle vector pLC544 was constructed by using randomly sheared segments of yeast DNA joined at the Bam HI site of the vector by poly(dA-dT) connectors.

Fractionations of DNAs and of restriction enzyme digests of plasmid DNAs were carried out in 1.2% agarose gels by using a horizontal gel apparatus. DNA blot hybridizations were carried out according to the methods of Southern by using plasmid DNA labeled in vitro by nick translation.

The TRP1 locus on chromosome IV of S. cerevesiae mapped approximately one centimorgan (cM) (map unit) from its centromere. The TRP1 gene specifies the production of the enzyme, N-(5'-phosphoribosyl)anthranilate isomerase in E. coli. This isomerase and indolyl-3-glycerol phosphate synthetase are part of the same 45kdal polypeptide chain specified by the trpC gene. However, E. coli mutants carrying the trpC1117 allele lack isomerase activity, but retain normal levels of the synthetase.

The mutant W3110 (trpC1117) was transformed with a pool of ColE1-DNA (yeast) hybrid plasmid DNA. (Chinault and Carbon (1979) Gene, 5 111–126) The Colicin E1-resistant Trp+ transformants obtained, carried either one of two hybrid plasmids with large regions of cloned yeast DNA. The following are the restriction maps of the two plasmids pYe(TRP1)54 and pYe(TRP1)74.

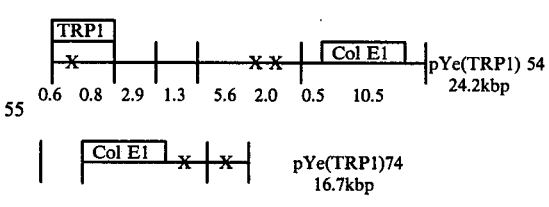

Location of EcoR1 (—|—) and HindIII (—X—) sites.

Plasmid pYe(TRP1)54 was restriction digested to completion with EcoR1 and mixed with EcoR1-cut ampicillin-resistant pBR313 DNA, and the DNAs ligated. When this mixture was used to transform E. coli W3110 (trpC1117) selecting for Trp+Amp$^R$, five of twelve transformants screened contained plasmids consisting of pBR313 and a single 1.45kbp EcoR1 fragment from pYe(TRP1)54. This small fragment was inserted into pBR313 DNA in both orientations.

The 1.45kbp DNA fragment in hybrid DNA molecules leads to high-frequency transformation of yeast and allows hybrid DNAs to replicate autonomously and to express both TRP1 and other structural genes in the absence of recombination into the host genome because of a replication origin included in the fragment.

A shuttle vector was prepared from pBR313-TRP1 and is referred to as pLC544. The shuttle vector pLC544 is characterized in that yeast strains transformed by the plasmid are unstable for the Trp+ character, that pLC544 replicates autonomously in the yeast nucleus and that the plasmid can be transmitted in matings and remains structurally unaltered by passage in yeast and by the processes of mating, meiosis, sporulation and germination. The plasmid has a selectable marker in yeast (TRP1) and four selectable markers in $E.\ coli$: Colicin-E1$^R$, TrpC+amp$^R$, tet$^R$ and single BamHI and SalI restriction sites into which foreign DNA may be introduced.

Randomly sheared segments of yeast DNA (8–12kbp in length) were annealed to pLC544 DNA at the BamHI site by using poly(dA-dT) connectors, and the DNA preparation used to transform $E.\ coli$ strain SF8, selecting for ampicillin resistance. After incubation for 24 hrs. at 37° C., approximately 9,000 small colonies were picked from the transformation plates. These were transferred to fresh plates in a grid array and ultimately transferred to microtiter dishes for permanent storage. Small colonies were picked from the original plates, because preliminary screening revealed they have the larger inserts. A hybrid plasmid DNA preparation was then purified from a pool of colonies in this collection.

Approximately 15 μg of the hybrid plasma DNA pool described above was used to transform yeast strain XSB52-23C(leu2 cdc10 trp1). Spheroplasts were plated in minimal SD agar with casamino acid (no tryptophan) and allowed to incubate at room temperature for 8 hrs. and then at the restrictive temperature (37° C.). After 48 hrs. one colony (of a total of 15,000Trp+ transformants) appeared and upon restreaking it continued to grow at 37° C. in the absence of tryptophan.

A crude preparation of total nucleic acid was isolated from the Trp+Cdc10+ transformant and used to transform $E.\ coli$ strain SF8, selecting for ampicillin resistance. Four transformants were thus obtained by using four $A_{260}$ units of the crude preparation and each contained the hybrid plasma pYe(CDC10)1. The gross structure of the vector had remained unchanged in the passage from $E.\ coli$ to yeast and back to $E.\ coli$. That the integrity of the yeast DNA insert had been maintained was confirmed by Southern blot hybridization with EcoRI-cut total yeast DNA and [$^{32}$P]-labeled pYe(CDC10)1 DNA. The failure of this probe to hybridize with other fragments, even weakly, in the autoradiogram, indicates the absence of extensive repeated sequences in the cloned DNA.

Two further plasmids were prepared. pYe(CDC10)1 DNA was restricted with BamH1, religated, transformed into $E.\ coli$ selecting for ampicillin resistance, followed by isolation of a new plasmid pYe(CDC10)1-1 that contains all the DNA of pYe(CDC10)1, except the 3.5kbp BamH1 fragment. In a second study, the 3.5kbp fragment was recloned at the BamH1 site of pLC544 to give plasmid pYe(CDC10)1-2. These two recloned plasma DNAs and that of the original pYe(CDC10)1 were utilized to transform yeast strain XSB52-23C(cdc10 trp2), selecting in each case for Trp+ and Trp+Cdc10+ transformants. As expected, all of these plasmids transformed yeast with high frequency, the original plasmid to Trp+Cdc10+, while the recloned plasmids to Trp+. The pYe(CDC10)1 also contains the yeast chromosomal replicator ars1.

In order to determine the behavior of the plasmid pYe(CDC10)1 the following experiments were carried out.

Strain XSB5223Cα/pYe(CDC10)1(cdc10 leu2 trp1/CDC10 TRP1) was crossed with X2928-30-1Aa(trp1 leu1 ade1 met14), diploids were sporulated and the resulting asci were dissected for genetic analysis. Data from 16 tetrads indicate that the plasmid (marked by the wild type TRP1 allele) in at least 60% of the asci is segregating in the first meiotic division as a chromosome and is thus found in the two sister spores, the products of the second meiotic division. Only parental ditype and nonparental ditype asci were obtained in this cross using as references the centromere markers leu1, leu2, met14, and ade1. Thus the TRP1 locus on the plasmid is behaving as a centromere-linked marker. The TRP1 gene on pYe(CDC10)1 is unlinked to ade1, cdc10, leu1, leu2, or met14 and is therefore not integrated on chromosomes I, III, VII or XI. The plasmid was completely lost in about 30% of the asci and in one ascus was found in all four spores, but did not segregate either 1+:3− or 3+:1− in any asci analyzed in this cross.

A second cross was carried out with one of the progeny of cross 1, SB17Aa/pYe(CDC10)1(cdc10 trp1 leu2 ade1/CDC10 TRP1), and strain 6204-18Aα (cdc10 leu2). Data similar to that from Cross 1 were obtained. The plasmid in Cross 2 is again segregating 2+:2− in the first meiotic division in 92% of the asci and is found in all four spores in one ascus. With ade1 as the reference centromere marker, again the marker scored on the plasmid (CDC10) in this cross) is centromere-linked. The plasmid marker, CDC10, is unlinked to chromosome IV, because in those tetrads where CDC10 segregated 2+:2−, TRP1 (wild type allele on both the minichromosome and one parental chromosome) segregated both 2+:2− and 4+:0−.

Backcrosses of plasmid-bearing progeny from Cross 1 with the original parents XSB52-23C and X2928-3D-1A gave the same pattern of 2+:2− segregation of the wild type plasmid marker that is independent of the segregation of markers on other chromosomes. In all the above crosses, the two markers on pYe(CDC10)1, CDC10 and TRP1 were linked in every ascus scored. No asci were obtained that consisted of 2 viable and 2 nonviable sister spores. Thus the minichromosome does not appear to pair with any of the other yeast chromosomes.

In order to locate the CDC10 gene on pYe(CDC10)1, two reclones of this plasmid had been constructed. The first, pYe(CEN3)11 (referred to as pYe(CDC10)1-1 above) contains all the yeast DNA in pYe(CDC10)1 cloned into pLC544, except the 3.5kbp BamHI fragment from the middle of the insert. The second, pYe35 (referred to above as pYe(CDC10)1-2) contains only this 3.5kbp BamHI restriction fragment and the vector pLC544. Neither plasmid complements the cdc10 mutation in yeast, which indicates that one of the two BamHI sites on pYe(CDC10)1 is probably close to or within the CDC10 gene. Both pYe(CEN3)11 and pYe35 DNAs transform Trp− yeast to Trp+ with high efficiency, since they contain a TRP1 ars1 vector. However, only one, pYe(CEN3)11, yields transformants that are all mitotically stable for the Trp+ phenotype.

When a mating was carried out between XSB52-23C/pYe(CEN3) 11(trp1 cdc10/TRP1) and X2928-3D-1A(trp1 ade1), data similar to that for crosses 1-4 (above) were obtained. In 60% of the asci 2+:2— segregation was observed for the TRP1 marker on pYe(CEN3)11. The minichromosome was lost entirely in 27% of the asci and in 13% was found in all four spores. Again only parental and non-parental ditype asci were obtained with respect to centromere reference markers, indicating centromere linkage of TRP1. No linkage of the minichromosome to chromosomes I or III was observed, since pYe(CEN3)11 segregated independently of the ade1 and cdc10 markers.

Based on comparisons of transformers, generated with different plasmids obtained by restriction of pYe(CDC10)1, the stabilizing or centromeric DNA (CEN3) is concluded to be contained in pYe(CEN3)11 (and pYe(CDC10)1) on the 1.6kbp segment which extends from the BamHI site to the end of the insert in the direction of the leu2 locus. To test this hypothesis, 1.6kbp yeast DNA segment was recloned into the plasmid, pGT12(LEU2 ars1) (Tschumper, G. and Carbon, J. Gene 10, 157–166 (1980)). The DNA segment was excised from pYe(CEN3)11 DNA with the enzymes BamHI and HindIII. This treatment yields a single BamHI-HindIII restriction fragment whose BamHI site is derived from the single BamHI site in pYe(CEN3)11 and whose HindIII site is derived from HindIII site in the vector (pLC544), located about 400 basepairs from the end of the insert of yeast DNA. The 1.6kbp segment of interest, which is thus included on a 2.0kbp BamHI-HindIII fragment, was then inserted into plasmid pGT12, also cut with a combination of BamHI and HindIII.

Plasmid pGT12 was constructed by inserting a 1.4kbp EcoRI restriction fragment containing TRP1 and ars1 (Stinchcomb et al. Nature 282, 39–43 (1979)) and a 2.2 PstI fragment containing the LEU2 gene into the single EcoRI and PstI sites of pBR322 (Tschumper and Carbon, supra). This plasmid also carried resistance to tetracycline. When the 2.0kbp CEN3 fragment is inserted into pGT12 cut with a combination of BamHI and HindIII, both tet$^R$ and TRP1 expression are destroyed, but the ars1 chromosomal replicator is left intact. The resulting plasmid, pYe(CEN3)41, thus carries both CEN3 and the replicator ars1 in addition to the LEU2 marker.

Plasmid pYe(CEN3)41 transforms strain XSB52-23C(leu2-3 leu2-112) to Leu+ with high frequency and is stable in the transformants. Its behavior in meiosis is essentially the same as that described for pYe(CDC10)1 and pYe(CEN3)11 in crosses 1-5. Thus the presence of the 1.6 kbp segment (CEN3) on a plasmid carrying a yeast chromosomal replicator is all that is required for the plasmid to behave as a chromosome in mitosis and meiosis in the majority of asci analyzed.

Genetic data in Crosses 1-6 confirm random assortment of CEN3 minichromosome with respect to chromosomes I, III, IV, and XI. The possibility that CEN3-containing plasmids are integrated near the centromere of one or several other yeast chromosomes was tested both biochemically and genetically. First a mating was performed between two minichromosome bearing progeny (Cross 7, Table I).

TABLE I

Meiotic segregation of the minichromosomes

| Genetic cross number | Minichromosome in cross | Minichromosome marker scored |
|---|---|---|
| 1 | pYe(CDC10)1 | TRP1 |
| 2 | pYe(CDC10)1 | CDC101 |
| 3 | pYe(CDC10)1 | TRP1 |
| 4 | pYe(CDC10)1 | TRP1 |
| 5 | pYe(CEN3)11 | TRP1 |
| 6 | pYe(CEN3)41 | LEU2 |
| 7 | pYe(CDC10)1 X pYe(CDC10)1 | TRP1 |
| 8 | pYe(CDC10)1 X pYe(CEN3)41 | TRP1 LEU2 |

| Genetic cross number | Distribution in tetrads of genetic marker on minichromosome (%) | | | | |
|---|---|---|---|---|---|
| | 4+:0— | 3+:1— | 2+:2— | 1+:3— | 0+:4— |
| 1 | 1(6%) | 0 | 10(63%) | 0 | 5(31%) |
| 2 | 1(8%) | 0 | 11 (92%) | 0 | 0 |
| 3 | 1(7%) | 0 | 11(79%) | 0 | 2(14%) |
| 4 | 4(21%) | 0 | 11(58%) | 0 | 4(21%) |
| 5 | 4(13%) | 0 | 9(60%) | 0 | 2(27%) |
| 6 | 3(14%) | 3(14%) | 13(62%) | 1(5%) | 1(5%) |
| 7 | 6(35%) | 0 | 9(53%) | 1(6%) | 1(6%) |
| 8 | 10(24%) | 1(2%) | 31(74%) | 0 | 0 |
| | 8(19%) | 2(5%) | 24(57%) | 0 | 8(19%) |

| Genetic cross number | Test for centromere linkage of marker on minichromosome | | | Reference centromere marker (Chromosome) |
|---|---|---|---|---|
| | PD | NPD | T | |
| 1 | 2 | 8 | 0 | met14(XI) |
| 2 | 2 | 8 | 1 | ade1(I) |
| 3 | 4 | 7 | 0 | met14(XI) |
| 4 | ND | ND | ND | — |
| 5 | 4 | 5 | 0 | ade1(I) |
| | 5 | 4 | 0 | cdc10(III) |
| 6 | 7 | 6 | 0 | trp1(IV) |
| | 7 | 5 | 0 | cdc10(III) |
| 7 | ND | ND | ND | — |
| 8 | 15 | 16 | 0 | met14(XI) |
| | 10 | 14 | 0 | met14(XI) |
| | 17 | 2 | 0 | TRP1(mini) |

In all the above crosses the marker used to follow the minichromosome was wild-type on the minichromosome and mutant in both parents. The crosses were: (1) XSB52-23cα/pYe(CDC10)1(cdc10 leu2-3 leu2-112 trp1 gal/CDC10 TRP1) with X2928-3D-1Aa(ade1 gal1 his2 leu1 met14 trp1 ura3); (2) SB17Aa/pYe(CDC10)1 (ade1 cdc10 leu2-3 leu2-112 met14 trp1/CDC10 TRP1) with 6204-18Aα(cdc10 thr4 leu2-3 leu2-112); (3) SB1Cα/pYe(CDC10)1(his2 leu1 met14 trp1/CDC10 TRP1) with XSB52-23Cα(cdc10 leu2-3 leu2-112 trp1 gal); (4) SB17Bα/pYe(CDC10)1 (ade1 cdc10 leu2-3 leu2-112 met14 trp1/CDC10 TRPL) with X2928-3D-1Aa; (5) XSB52-23Cα/pYe(CEN3)11 with X2928-3D-1Aa; (6) XSB52-23Cα/pYe(CEN3 41 with X3144-1Da(ade2 arg9 can1 his2 his6 leu2 pet8 trp1); (7) SB14Ba/pYe(CDC10)1 (ade1 his2 trp1/CDC10 TRP1) with SB17Bα/pYe(CDC10)1(ade1 cdc10 leu2-3 leu2-112 met14 trp1/CDC10 TRP1); (8) SXB52-23Cα/pYe(CEN3)41 with SB17Aa/pYe(CDC10)1.

Transformation of yeast in the presence of polyethylene glycol results in a high proportion of diploid transformants (a/a or α/α). Diploids are easily recognized by the extremely low spore viability obtained when they are crossed with a haploid, and in this way were eliminated from the group of haploid transformants used in the above crosses.

PD=parental ditype; NPD=nonparental ditype; T=tetratype; ND=not determined.

In the majority of asci in Cross 7, the minichromosomes (both TRP1) show the 2+:2− segregation pattern, indicating that the minichromosomes are frequently going to the same pole in the first meiotic division and are thus not pairing with each other all the time, if at all. This segregation pattern also confirms that pYe(CDC10)1 is not integrated into any other single chromosome in the parents in this cross. If it were, all daughter spores should contain plasmid, because the chromosome pair into which the plasmid is integrated would duplicate in meiosis I and go to opposite poles. This point is again confirmed in Cross 8 where the minichromosomes are individually marked. In at least two asci both minichromosomes went to the same pole in meiosis I and were therefore both found in the same two sister spores.

The absence of asci with 2 viable and 2 nonviable sister spores in crosses 1–6 indicates that the minichromosomes are not pairing at the first meiotic division with any of the seventeen yeast chromosomes. Cross 8 (Table I and other data not shown) was performed with two strains, each harboring a CEN3 ars1 plasmid marked with either LEU2 or TRP1. Both parents in Cross 8 have mutations at both leu2 and trp1, therefore the behavior of each minichromosome can easily be followed individually. Based on detailed analysis of Cross 8 of data which is not shown, the following conclusions can be drawn. Each plasmid individually exhibited the 2+:2− segregation pattern in greater than 60% of the 42 tetrads examined. In the 19 asci where both plasmids segregated 2+:2−, the minichromosomes went to the same pole in the first meiotic division in 2 asci and to opposite poles in 17 asci. These numbers support the notion that the minichromosomes do not always pair, but there may be some preference to go to opposite poles in the first division. They seem to segregate randomly and independently with respect to one another, and all combinations of 4+:0−, 2+:2−, and 0+:4− are seen. Both minichromosomes were found in all four spores in 3 tetrads; in 5 tetrads pYe(CEN3)41 was found in all four spores, but pYe(CDC10) segregated 2+:2−; in 3 asci pYe(CDC10)1 was in all four spores, but pYe(CEN3)41 was completely lost. Thus two minichromosomes together in a sporulating diploid show the same meiotic behavior as either one exhibits alone.

The data indicate that cdc10 is located about 3 kbp from the centromere on the right arm of chromosome III. There are approximately 25 kbp of DNA between the LEU2 and CDC10 genes. The genetic map distance between leu2 and centromere is about 8 cM. Thus there is an average of about 3kbp/cM from leu2 across the centromere to cdc10. This number is close to the 2.7 kbp/cM (Strathern et al, Cell 18, 309–319 (1979)) for very large distances on the circular chromosome III, indicating that the centromere does not appreciably distort recombination frequencies in the leu2-cdc10 region.

Within the limits of a standard Southern blot hybridization, plasmid pYe(CDC10)1 contains only unique DNA. By this same criteron, all the DNA between leu2 and cdc10 is unique DNA.

The small circular chromosomes that have been constructed around the CEN3 element have many properties that mimic those of the much larger parental chromosomes. They are stable both in mitosis and through the first and second divisions of meiosis, probably because CEN3 is providing an attachment site for spindle structures, a site that may be unique for each chromosome. A chromosomal replicator must accompany the CEN3 segment to permit proper centromere function, but the replicator alone, or a combination of chromosomal replicators, do not stabilize a plasmid. Therefore the minichromosomes, like the larger chromosomes, require both an attachment site and one or more replicators. Unlike the parental chromosomes, the small circular chromosomes do not always pair, but, as is the case in sporulating aneuploid yeast strains, absence of pairing does not prevent the chromosomes from segregating in meiosis.

The CEN3 minichromosomes are excellent probes for the study of events in mitosis and meiosis, particularly with regard to the protein-nucleic acid interactions occurring between the centromere and the mitotic and meiotic spindle structures. Minichromosomes with a functional centromere will be useful as well for studies of chromatin structure and the organization of DNA-associated proteins in the centromere region.

Finally, the mitotic stability of CEN3 plasmids make them especially suitable cloning vehicles. Studies of expression of cloned genes on minichromosomes would not be complicated by the variable mitotic stability displayed by other vectors constructed for cloning in yeast. The functional centromeric DNA sequence, CEN3, is not altered by propagation in E. coli, since all the CEN3 minichromosomes were originally isolated in that bacterium before being put into yeast.

The subject minichromosomes provide stable maintenance of exogenous genes in eukaryotic cells, allowing for continued replication of the minichromosomes through many generations of the cells and stable expression of the functional genes included in the minichromosomes. In this way, eukaryotic cells can be used for the production of a wide variety of proteinaceous as well as other organic products. In addition, the minichromosomes can be introduced into cells to stably complement auxotrophic properties or provide unique properties exogenous to the transformed host.

Although the foregoing invention has been described in some detail by way of illustration and example for purposes of clarity of understanding, it will be obvious that certain changes and modifications may be practiced within the scope of the appended claims.

What is claimed is:

1. DNA having less than 10% of the base pairs of a yeast chromosome, having the same DNA sequence capable of replication and stable mitotic maintenance in a yeast host comprising a DNA segment coding for centromere-like activity during mitosis of said yeast host and a DNA sequence coding for a replication site recognized by said yeast host.

2. DNA according to claim 1, wherein said DNA segment coding for centromere-like activity is fewer than 2kbp.

3. A yeast host containing a DNA fragment derived from a yeast chromosome having centromere-like activity, having fewer than 10% of the base pairs of a yeast chromosome having the same DNA sequence and imparting mitotic stability joined to an ars gene.

* * * * *